United States Patent
Luo et al.

(10) Patent No.: US 11,145,850 B2
(45) Date of Patent: Oct. 12, 2021

(54) SOFT NEURAL ELECTRODE BASED ON THREE-DIMENSIONAL POROUS GRAPHENE FOAM MATERIAL AND USE OF THREE-DIMENSIONAL POROUS GRAPHENE FOAM MATERIAL TO PREPARE BONE DEFECT FILLER

(71) Applicant: SOOCHOW UNIVERSITY, Suzhou (CN)

(72) Inventors: Judong Luo, Suzhou (CN); Qi Zhang, Suzhou (CN); Yuyou Qiu, Suzhou (CN); Shuyu Zhang, Suzhou (CN); Qin Song, Suzhou (CN); Guangyu Tang, Suzhou (CN); Jianping Cao, Suzhou (CN); Hua Jiang, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 59 days.

(21) Appl. No.: 16/320,141

(22) PCT Filed: May 10, 2017

(86) PCT No.: PCT/CN2017/083737
§ 371 (c)(1),
(2) Date: Jan. 24, 2019

(87) PCT Pub. No.: WO2017/219776
PCT Pub. Date: Dec. 28, 2017

(65) Prior Publication Data
US 2020/0185703 A1    Jun. 11, 2020

(30) Foreign Application Priority Data

Jun. 22, 2016  (CN) .......................... 201610453656.8
Jul. 28, 2016  (CN) .......................... 201610598554.5

(51) Int. Cl.
*H01M 4/133* (2010.01)
*A61N 1/05* (2006.01)
(Continued)

(52) U.S. Cl.
CPC ............. *H01M 4/133* (2013.01); *A61L 27/56* (2013.01); *A61N 1/0551* (2013.01); *H01M 4/808* (2013.01); *A61L 2430/02* (2013.01)

(58) Field of Classification Search
None
See application file for complete search history.

(56) References Cited

U.S. PATENT DOCUMENTS

2006/0200217 A1*  9/2006  Wessman ................. A61N 1/05
                                                                  607/116
2012/0076830 A1    3/2012  Sitharaman
(Continued)

FOREIGN PATENT DOCUMENTS

CN         101617965 A      1/2010
CN         102716514 A     10/2012
(Continued)

*Primary Examiner* — Dominic Lazaro
(74) *Attorney, Agent, or Firm* — SZDC Law PC

(57) ABSTRACT

The invention provides a neural electrode, including a current generation device, a first and a second electrode. The current generation device is connected to the first and second electrodes through a conductive metal wire respectively. At least one of the first and second electrodes is a graphene electrode. The graphene electrode has soft texture and desirable stability to tolerate the repeated pressing and folding treatment, very high charge injection efficiency, and desirable in vivo stability, and is configured to electrically stimulate tissues and organs such as hearts and nerves to promote electrical stimulation and repair of neurons, to further promote regeneration of neural functions. The invention further provides use of a mineralized three-dimensional porous graphene foam material to prepare a bone defect (Continued)

filler. The bone defect filler has desirable biological compatibility, promotes cell proliferation, and accelerates and induces osteogenic differentiation of bone marrow mesenchymal stem cells.

7 Claims, 2 Drawing Sheets

(51) Int. Cl.
*H01M 4/80* (2006.01)
*A61L 27/56* (2006.01)

(56) References Cited

U.S. PATENT DOCUMENTS

| | | |
|---|---|---|
| 2013/0090542 A1 | 4/2013 | Kipke et al. |
| 2014/0068935 A1* | 3/2014 | Li .................. H01R 13/6599 29/876 |
| 2014/0110049 A1* | 4/2014 | Yuen .................. H01L 23/373 156/280 |

FOREIGN PATENT DOCUMENTS

| | | | |
|---|---|---|---|
| CN | 102824689 A | 12/2012 | |
| CN | 103751850 A | 4/2014 | |
| CN | 104078248 A | 10/2014 | |
| CN | 105999397 A | 10/2016 | |
| CN | 106139388 A | 11/2016 | |
| CN | 206228767 A | 6/2017 | |
| WO | 2010107720 A2 | 9/2010 | |
| WO | WO-2013180661 A1 * | 12/2013 | ............. H01G 11/36 |

\* cited by examiner

SOFT NEURAL ELECTRODE BASED ON THREE-DIMENSIONAL POROUS GRAPHENE FOAM MATERIAL AND USE OF THREE-DIMENSIONAL POROUS GRAPHENE FOAM MATERIAL TO PREPARE BONE DEFECT FILLER

This application is the National Stage Application of PCT/CN2017/083737, filed on May 10, 2017, which claims priority to Chinese Patent Application No.: 201610453656.8, filed on Jun. 22, 2016, and Chinese Patent Application No.: 201610598554.5, filed on Jul. 28, 2016, all of which are incorporated by reference for all purposes as if fully set forth herein.

FIELD OF THE INVENTION

The present invention relates to the field of biomedical engineering, and in particular, to a neural electrode based on a three-dimensional porous graphene foam material and a preparation method of the same and use of a three-dimensional porous graphene material to prepare a bone defect filler.

DESCRIPTION OF THE RELATED ART

A basic functional unit of neural activity is a neuron which has the functions of receiving a stimulus and conducting an impulse and excitation. In electrical stimulation therapy, an electrical signal having a suitable waveform and frequency is applied to a neural electrode to stimulate a neural tissue in direct contact to activate neural activity, to alleviate a dysfunction in a neural system. A pacemaker is an electrotherapeutic instrument implanted in a body. A pulse generator outputs an electrical pulse powered by a battery. A lead electrode conducts the electrical pulse to stimulate myocardium in contact with the electrode, to excite and contract the heart, to treat some cardiac dysfunctions caused by irregular heartbeats.

A conventional metal wire electrode such as platinum, gold, and titanium has been developing remarkably, but still has the following problems: (1) A rigid electrode material and a soft tissue have very different mechanical performance, such that it is difficult to match the mechanical difference between an electrode material and a soft tissue. (2) The charge injection efficiency is low. (3) The biological compatibility is poor. The development of a novel electrode material is significant for the clinical use of an implantable neural electrode.

A bone defect means that the structural integrity of a bone is compromised and is a common clinical disease. The major causes to bone defects include injuries, infections, tumors, surgical debridement of osteomyelitis, and various congenital disorders. When a bone defect is excessively severe or a bone defect occurs on a relatively small bone, such a bone defect heals slowly and poorly, and surgical intervention is required. Artificial bone filling is one of the major therapies. The most basic requirement on artificial bone filling is desirable biological compatibility, so that immunological rejection responses do not occur.

Graphene is a novel carbon allotropy following the discovery of fullerene and carbon nanotubes. Graphene has a unique physical-chemical structure and a unique electronic structure. Therefore, graphene manifests various remarkable performances that conventional materials do not have. For example, graphene has features such as an ultra-large theoretical specific surface area, desirable electrical and thermal conductivity, and excellent mechanical performance, optical performance, and biological compatibility. Three-dimensional porous graphene inherits the excellent properties of two-dimensional graphene and has a larger specific surface area and provides diverse opportunity for further chemical surface modification.

Hydroxyapatite is one of the major inorganic components of bones and is widely applied to bone tissue engineering. Three-dimensional porous graphene and hydroxyapatite are combined so that a mineralized material has a simulation bone structure, promotes cell proliferation, and accelerates and induces osteogenic differentiation of bone marrow mesenchymal stem cells.

SUMMARY OF THE INVENTION

To solve the foregoing technical problem, the present invention provides a soft neural electrode based on a three-dimensional porous graphene foam material and a preparation method of the same. The neural electrode has high charge injection efficiency and desirable biological compatibility. The present invention further provides use of a three-dimensional porous graphene material to prepare a bone defect filler and a bone defect filler. The bone defect filler has desirable biological compatibility, promotes cell proliferation, and accelerates and induces osteogenic differentiation of bone marrow mesenchymal stem cells.

To achieve the foregoing object, the following technical solutions are used in the present invention.

In an aspect, the present invention provides a soft neural electrode based on a three-dimensional porous graphene foam material, including a current generation device, a first electrode and a second electrode. The current generation device is connected to the first electrode and the second electrode through a conductive metal wire respectively. At least one of the first electrode and the second electrode is a three-dimensional porous graphene electrode. The graphene electrode is configured as a disc or a strip.

Preferably, an insulating protective sleeve is disposed outside the conductive metal wire.

More preferably, the protective sleeve is made of silica gel or polyurethane, and the thickness of the protective sleeve is between 0.5 mm and 3 mm. Preferably, the conductive metal wire is a silver wire or a copper wire, and is more preferably a silver wire.

Preferably, the conductive metal wire is connected to the three-dimensional porous graphene electrode by a conductive adhesive, and is more preferably a silver adhesive.

Preferably, the three-dimensional porous graphene electrode is provided with a protective substrate.

Preferably, the protective substrate is formed of a polymer material, and the polymer material is polydimethylsiloxane (PDMS), polyurethane or a polyacrylic acid copolymer, and is more preferably PDMS.

Preferably, the thickness of the protective substrate is 0.1 mm to 2 mm.

Preferably, a thickness ratio of the three-dimensional porous graphene electrode to the protective substrate is 1:0.25 to 4. The protective substrate is placed onto one surface of electrode. The other surface of electrode is unprotected and the graphene foam material is exposed to avoid the harm of electrical conductivity.

In another aspect, the present invention provides a preparation method of the foregoing neural electrode based on a three-dimensional porous graphene foam material, including the steps of:

(1) bonding a three-dimensional porous graphene electrode to a conductive metal wire by a conductive adhesive, and curing the conductive adhesive completely;

(2) immersing a connecting portion of the conductive metal wire and the three-dimensional porous graphene electrode in a polymer solution, and curing the polymer to prepare a protective substrate, where a polymer material in the polymer solution is selected from polydimethylsiloxane (PDMS), polyurethane or a polyacrylic acid copolymer, and is preferably PDMS; and (3) connecting the three-dimensional porous graphene electrode having the protective substrate and another electrode to a current generation device through a conductive metal wire respectively, to prepare a neural electrode.

Graphene is a novel carbon nanomaterial following the discovery of fullerene and carbon nanotubes. Graphene has a unique physical-chemical structure and a unique electronic structure. Therefore, graphene manifests various remarkable performances that conventional materials do not have. For example, graphene has features such as an ultra-large theoretical specific surface area, desirable electrical and thermal conductivity, and excellent mechanical performance, flexibility and elasticity (extensibility of nearly 20%), optical performance, as well as biological compatibility. Three-dimensional porous graphene inherits the excellent inherent properties of two-dimensional graphene and has a larger specific surface area and provides diverse opportunity for further chemical surface modification. Therefore, a neural electrode based on three-dimensional porous graphene foam is constructed to apply electrical stimulation and treat diseases, to further improve the quality of life of patients, and very high economic value is obtained.

By means of the foregoing technical solution, the present invention at least has the following advantages:

The present invention provides a flexible and soft neural electrode based on a three-dimensional porous graphene material and a fabrication method of the same. The soft neural electrode includes a three-dimensional porous graphene electrode, so that electrical stimulation can be applied to local regions of tissues and organs. The neural electrode has a three-dimensional network structure with a high specific surface area, and has soft texture and desirable stability to tolerate the repeated pressing and folding treatment, so that the neural electrode can be curled and used. The neural electrode has very high charge injection efficiency, and is configured to electrically stimulate tissues and organs such as hearts and nerves to promote electrical stimulation and repair of neurons, to further promote restoration of neural functions. The neural electrode has desirable biological compatibility, and a cell survival rate is high when neurons or neural stem cells are cultured on the surface. The neural electrode has desirable in vivo stability.

In another aspect, the present invention provides use of a three-dimensional porous graphene material to prepare a bone defect filler, where the three-dimensional porous graphene material is a mineralized three-dimensional porous graphene material.

Preferably, a mole ratio of carbon, calcium, and phosphorus in the mineralized three-dimensional porous graphene material is 1:0.05:0.03 to 1:500:300. The mole ratio is preferably 1:0.5:0.3 to 1:50:30. The mole ratio is further preferably 1:1:0.6 to 1:10:6.

Preferably, a hole diameter of the mineralized three-dimensional porous graphene material is 100 μm to 300 μm, the porosity of the mineralized three-dimensional porous graphene material is 99.3±0.5%, and a frame width forming a three-dimensional void is 100 μm to 200 μm.

Preferably, the coverage of hydroxyapatite in the mineralized three-dimensional porous graphene material is 90% to 100%.

Preferably, particle sizes of the hydroxyapatite are between 5 nm and 50 μm.

In still another aspect, the present invention also provides a preparation method of the foregoing bone defect filler, including the following steps:

(1) covering a three-dimensional porous graphene support with a filter paper, and performing mineralization processing, to obtain a mineralized three-dimensional porous graphene material;

(2) immersing the mineralized three-dimensional porous graphene material in a solution to freeze the mineralized three-dimensional porous graphene material;

(3) cutting the frozen mineralized three-dimensional porous graphene material into mineralized three-dimensional porous graphene sheets; and (4) immersing the mineralized three-dimensional porous graphene sheets in ethanol, and drying and sterilizing the three-dimensional porous graphene sheets to obtain the bone defect filler.

Preferably, single mineralized three-dimensional porous graphene sheet is used as the bone defect filler, or a plurality of mineralized three-dimensional porous graphene sheets are stacked and used as the bone defect filler.

Preferably, the plurality of mineralized three-dimensional porous graphene sheets are stacked by bonding using a biomedical adhesive.

Preferably, in the step (2), the solution is selected from water, tert-Butyl alcohol or a combination thereof.

Preferably, in the step (2), the mineralized three-dimensional porous graphene material is immersed in the solution and frozen at a temperature of −20° C. to −0.1° C.

Preferably, in the step (3), the frozen mineralized three-dimensional porous graphene material is cut at a temperature of −20° C. to 5° C. to ensure an intact form of the three-dimensional porous graphene material.

By means of the foregoing solutions, the present invention at least has the following advantages:

The present invention provides use of a mineralized three-dimensional porous graphene material to prepare a bone defect filler and a preparation method. Hydroxyapatite in a prepared mineralized three-dimensional porous graphene material has uniform particles, and there is no accumulation of excessively large particles. According to a filling requirement, a prepared mineralized three-dimensional porous graphene sheet is separately used or the prepared mineralized three-dimensional porous graphene sheets are stacked and used for filling various bone defects. The mineralized three-dimensional porous graphene sheets are soft as filling substances, have high porosity, and there are inorganic components that are the same as those forming a bone structure on the surface to simulate a bone structure, and can promote cell proliferation, and accelerate and induce osteogenic differentiation of bone marrow mesenchymal stem cells.

DETAILED DESCRIPTION OF THE PREFERRED EMBODIMENTS

Figure 1:
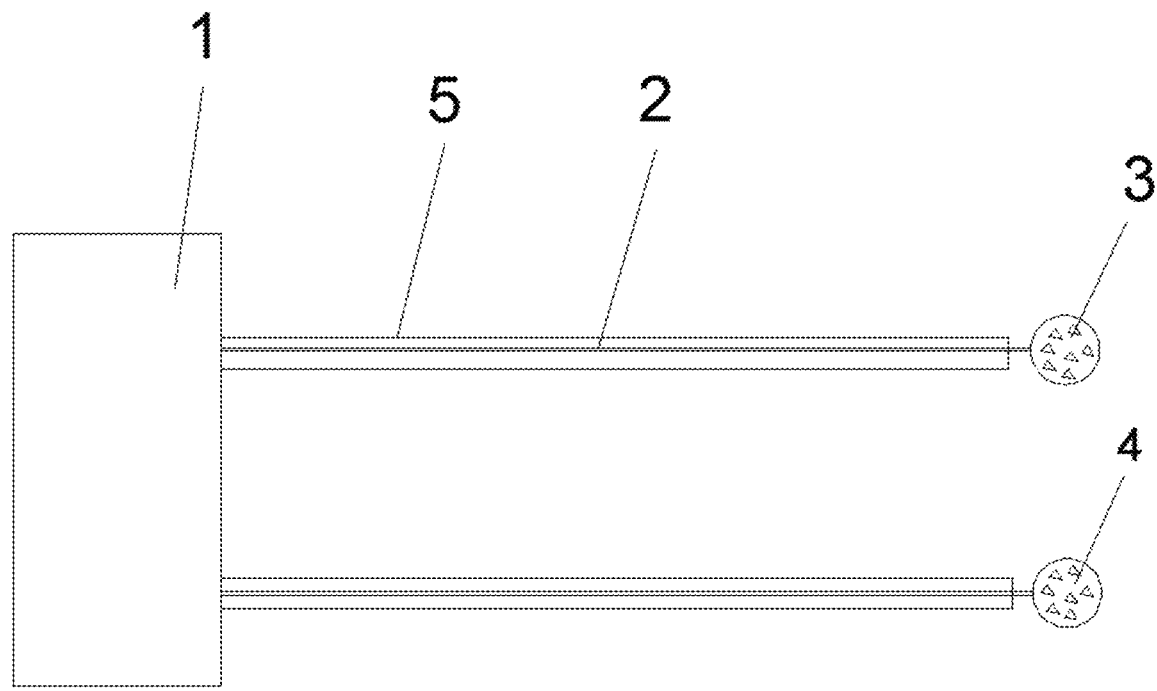
FIG. 1 is a schematic view of a neural electrode based on a three-dimensional porous graphene material according to the present invention.
Figure 2:
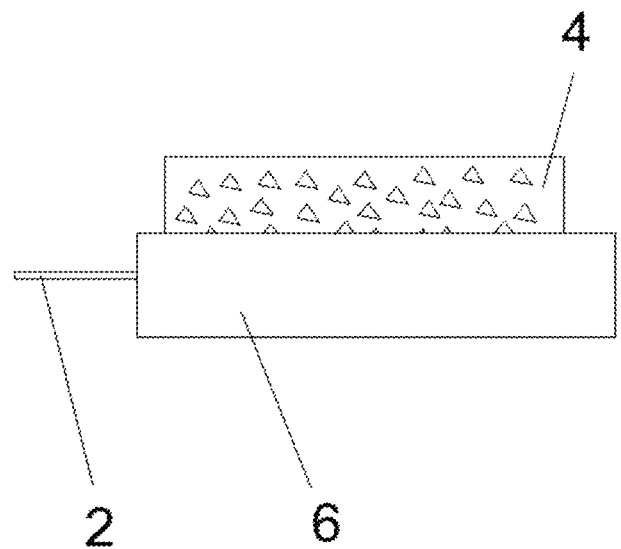
FIG. 2 is a schematic view of a three-dimensional porous graphene electrode and a protective substrate according to the present invention.

The present invention will be explained in more detail below with reference to the drawings and in connection with embodiments. It should be understood that, the exemplary embodiments and description thereof of the invention are used for illustrating the present invention and are not intended to limit the invention Referring to FIG. 1 and FIG. 2, a neural electrode in a preferred embodiment of the present invention includes a current generation device 1, a first electrode 3 and a second electrode 4. The current generation device 1 is connected to the first electrode 3 and the second electrode 4 through a conductive metal wire 2 respectively. At least one of the first electrode 3 and the second electrode 4 is a graphene electrode. The second electrode 4 is a graphene electrode in this embodiment. The graphene electrode has a disc or a strip shape.

To increase a specific surface area and improve a charge injection rate and stability, the graphene electrode 4 is a three-dimensional porous graphene electrode.

To avoid potential safety hazards, an insulating protective sleeve 5 is disposed outside the conductive metal wire 2.

Preferably, the protective sleeve 5 is silica gel or polyurethane, and the thickness of the protective sleeve 5 is between 0.5 mm and 3 mm.

Preferably, the conductive metal wire 2 is a silver wire or a copper wire, and is preferably a silver wire.

Preferably, the conductive metal wire 2 is connected to the three-dimensional porous graphene electrode by a conductive adhesive, and is preferably a silver adhesive.

To support the three-dimensional porous graphene electrode 4 and protect the conductive connecting surface of the conductive metal wire 2, the silver adhesive and the three-dimensional porous graphene electrode 4, a protective substrate 6 is disposed on one surface of the three-dimensional porous graphene electrode 4. The other surface of electrode is unprotected and the graphene is exposed. The conductive connecting surface is connected with and supported by the protective substrate 6.

Preferably, the protective substrate 6 is formed of a polymer material. The polymer material is polydimethylsiloxane (PDMS), polyurethane or a polyacrylic acid copolymer, and is preferably PDMS.

Preferably, the thickness of the protective substrate 6 is 0.1 mm to 2 mm.

If the thickness of protective substrate in the three-dimensional porous graphene electrode 4 is excessively large, the three-dimensional porous graphene electrode 4 is not soft enough and heavy and thus has poor usability. If the protective substrate 6 is thin, the three-dimensional porous graphene electrode 4 is not firm and cannot completely prevent the graphene electrode 4 from contacting with a tissue. If the protective substrate 6 fully covered onto the graphene foam material, making the graphene material insulated with the tissues and organs. The electrode 4 cannot work properly. Therefore, a thickness ratio of the three-dimensional porous graphene electrode 4 to the protective substrate 6 is 1:0.25 to 4.

Embodiment 1

Preparation of a neural electrode based on a three-dimensional porous graphene material includes the following steps:

(1) A three-dimensional porous graphene electrode 4 was bonded to a silver wire by a silver adhesive, and then was heated to 70° C. such that the silver adhesive was completely cured, wherein the thickness of the three-dimensional porous graphene electrode 4 is 0.5 mm.

(2) A connecting portion of the silver wire and the three-dimensional porous graphene electrode 4 was immersed in a PDMS solution, vacuuming was performed to remove bubbles from the solution, and the temperature was kept at 70° C. for 6 h to cure PDMS, then a protective substrate 6 with a thickness of 2 mm was prepared. Around 0.2 mm of graphene foam material was exposed and 0.3 mm (0.5-0.2=0.3 mm) of graphene foam material was protected with PDMS.

(3) The three-dimensional porous graphene electrode 4 with the protective substrate 6 and a metal titanium electrode were connected to a current generation device 1 through a silver wire respectively, and then a neural electrode was obtained.

Embodiment 2

Preparation of a neural electrode based on a three-dimensional porous graphene material includes the following steps:

(1) A three-dimensional porous graphene electrode 4 was bonded to a copper wire by a silver adhesive, and then was heated to 50° C. such that the silver adhesive was completely cured, wherein the thickness of the three-dimensional porous graphene electrode 4 is 2 mm.

(2) A connecting portion of the copper wire and the three-dimensional porous graphene electrode 4 was immersed in a PDMS solution, vacuuming was performed to remove bubbles from the solution, and the temperature was kept at 100° C. for 1 h to cure PDMS, then a protective substrate 6 with a thickness of 0.5 mm was prepared. 1.5 mm of graphene foam was exposed. Before PDMS is cured, a heart-shaped mold may be lightly pressed on a graphene surface, to produce a heart-shaped deformation on the graphene surface. After PDMS is completely cured, a concave electrode is obtained to better fit a heart region.

(3) The three-dimensional porous graphene electrode 4 with the protective substrate 6 and a metal platinum electrode were connected to a current generation device 1 through a copper wire respectively, and then a neural electrode was obtained.

Embodiment 3

Preparation of a neural electrode based on a three-dimensional porous graphene material includes the following steps:

(1) A three-dimensional porous graphene electrode was bonded to a silver wire by a silver adhesive, and then was heated to 60° C. such that the silver adhesive was completely cured, wherein the thickness of the three-dimensional porous graphene electrode 4 is 1 mm.

(2) A connecting portion of the silver wire and the three-dimensional porous graphene electrode 4 was immersed in a polyurethane solution, vacuuming was performed to remove bubbles from the solution, the solution was placed at a room temperature for 24 h to cure polyurethane, wherein a protective substrate with a thickness of about 1 mm was prepared. And 0.5 mm of graphene foam was exposed.

(3) The three-dimensional porous graphene electrode 4 with the protective substrate 6 and a metal gold electrode were connected to a current generation device 1 through a silver wire respectively, and then a neural electrode was obtained.

Embodiment 4

Preparation of a neural electrode based on a three-dimensional porous graphene material includes the following steps:

(1) Two three-dimensional porous graphene electrodes were bonded to silver wires by a silver adhesive respectively, and then were heated to 60° C. such that the silver adhesives were completely cured, wherein the thickness of each three-dimensional porous graphene electrode 4 is 1 mm.

(2) A connecting portion between one of the silver wires and the three-dimensional porous graphene electrode 4 was immersed in a pre-polymer solution of polyacrylic acid, vacuuming was performed to remove bubbles from the solution, the solution was irradiated under ultraviolet light (10 W) for 6 h to cure polyacrylic acid, where the thickness of an obtained protective substrate 6 is approximately 1 mm. And 0.5 mm of graphene foam was exposed.

(3) The three-dimensional porous graphene electrode 4 with the protective substrate 6 and the other three-dimensional porous graphene electrode were connected to a current generation device 1 through a silver wire respectively, and then a neural electrode was obtained.

The neural electrode of the present invention has the following working principles:

The prepared flexible neural electrode based on three-dimensional porous graphene is applied to cardiac pacemaker. In the soft and flexible neural electrode based on three-dimensional porous grapheme, one electrode is a three-dimensional porous graphene electrode 4, and another is a metal titanium electrode. The three-dimensional porous graphene electrode 4 is implanted in a human's heart for exerting an electrical pulse to the heart to stimulate the heart to beat. The surface of exposed graphene foam is faced to the heart. The metal titanium in a metal titanium electrode may alternatively be platinum or gold. The metal titanium electrode may also alternatively a three-dimensional porous graphene electrode 4.

The prepared flexible neural electrode based on three-dimensional porous graphene may further be wound on a nerve for use. A typical use process is as follows: a surgery is performed to expose a nerve, and then a three-dimensional porous graphene electrode 4 in a strip form is lightly wrapped on the nerve. The surface of exposed graphene foam is faced to the nerve. The surgery should be performed as lightly as possible to avoid fracture of graphene, and then the cut tissue is stitched.

After testing, the flexible neural electrode based on three-dimensional porous graphene foam has the following effects: a charge injection amount in a unit area is 3 to 100 times that of a conventional electrode. When nerve cells are cultured on the surface, a cell survival rate is higher than 90%. An end surface of graphene may be curled for use. After graphene is curled by 100 times, a resistance change is less than 50%. After graphene is implanted in a body, a resistance change is less than 200% in three months.

Embodiment 5

The preparation of a mineralized three-dimensional porous graphene foam material includes the following steps:

(1) Three-dimensional porous graphene foam material was fabricated by chemical vapor deposition (CVD) with three-dimensional porous nickel as catalyst. After removing the nickel catalyst, and a three-dimensional porous graphene foam scaffold was obtained.

(2) $O_2$ plasma treatment was performed on the three-dimensional porous graphene scaffold for 3 min to 5 min, and then the three-dimensional porous graphene scaffold was covered with a filter paper.

(3) 2 mmol to 100 mmol bicarbonate ions were added to a simulated body fluid with a tenfold concentration (the simulated body fluid with a tenfold concentration is formed of compounds such as NaCl, $CaCl_2$, $MgCl_2$, $NaHCO_3$ and $Na_2HPO_4$), filtering was performed by using a filtering system with a 0.22 μm hole diameter, then the three-dimensional porous graphene support was placed on a decoloring shaker for 1 h to 12 h at a room temperature, and a mineralized three-dimensional porous graphene material was obtained, and finally the mineralized three-dimensional porous graphene material was washed with water and ethanol.

A mole ratio of carbon, calcium and phosphorus in the mineralized three-dimensional porous graphene material is 1:0.05:0.03 to 1:500:300. The mole ratio is preferably 1:0.5:0.3 to 1:50:30. The mole ratio is further preferably 1:1:0.6 to 1:10:6. A hole diameter of the mineralized three-dimensional porous graphene material is 100 μm to 300 μm. The porosity of the mineralized three-dimensional porous graphene material is 99.3±0.5%. A frame width forming a three-dimensional void is 100 μm to 200 μm. The coverage of hydroxyapatite in the mineralized three-dimensional porous graphene material is 90% to 100%. Particle sizes of the hydroxyapatite are between 5 nm and 50 μm. The mineralized three-dimensional porous graphene material was characterized by scanning electron microscope.

Figure 3:
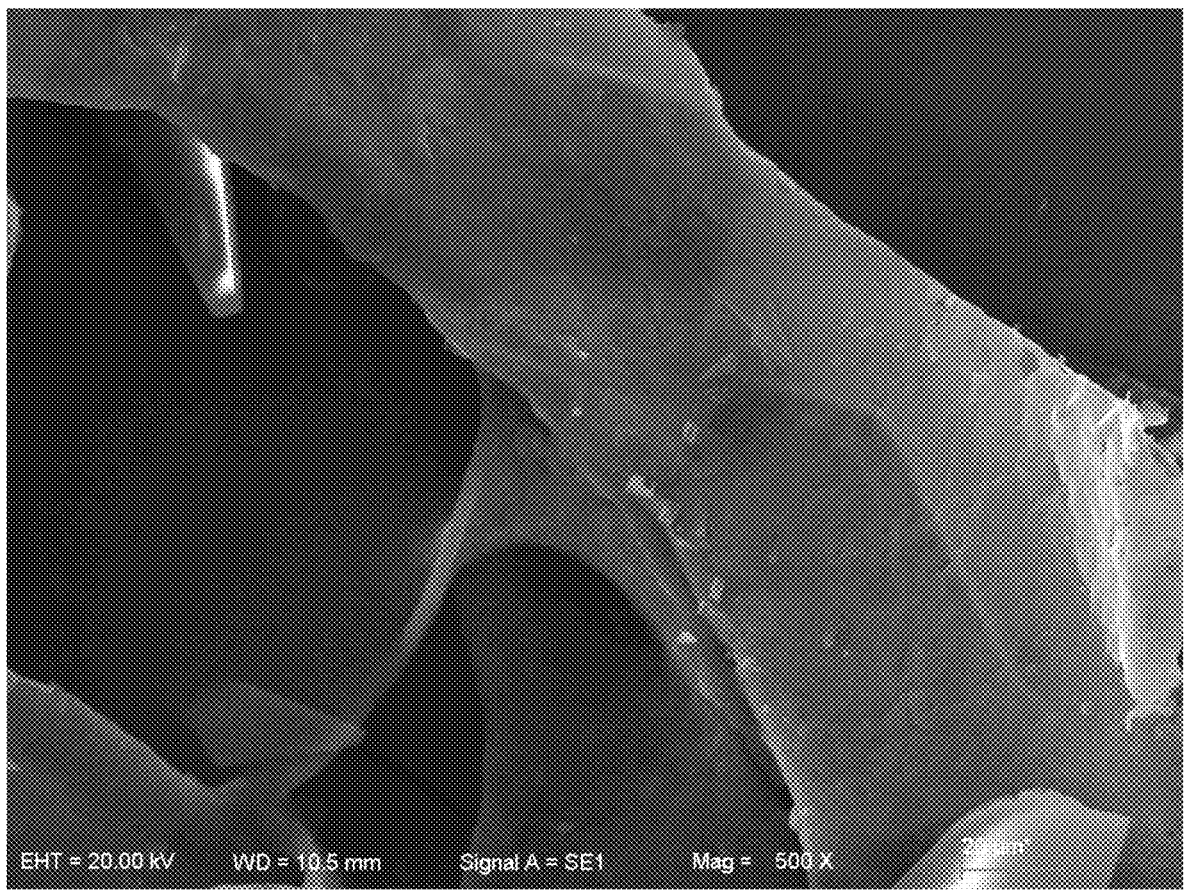
FIG. 3 is a scanning electron microscope image of mineralized graphene according to the present invention.

Specifically, 10 mmol bicarbonate ions were added to a simulated body fluid with a tenfold concentration, and the simulated body fluid is then placed for 4 h, and a mole ratio of carbon, calcium and phosphorus in the obtained mineralized three-dimensional porous graphene material is 1:0.5:0.3 to 1:2:1.2. The coverage of hydroxyapatite in the mineralized three-dimensional porous graphene material is 90% to 95%. Particle sizes of the hydroxyapatite are between 5 nm and 1 μm, and the porosity of the hydroxyapatite is 99.3±0.5%. The obtained material is shown in FIG. 3. The crystal in FIG. 3 shows that the three-dimensional porous graphene support is successfully mineralized.

100 mmol bicarbonate ions were added to the simulated body fluid with a tenfold concentration, and the simulated body fluid is then placed for 0.5 h, and a mole ratio of carbon, calcium and phosphorus in the obtained mineralized three-dimensional porous graphene material is 1:5:3 to 1:20:12. The coverage of hydroxyapatite in the mineralized three-dimensional porous graphene material is 95% to 100%. Particle sizes of the hydroxyapatite are mostly between 50 nm and 20 μm. Some particles of the hydroxyapatite agglomerate, particle sizes of agglomerated particles are about 50 μm, and the porosity of the hydroxyapatite is 98±1%.

Embodiment 6

Preparation of a bone defect filler using a mineralized three-dimensional porous graphene material.

The mineralized three-dimensional porous graphene material of the embodiment 5 was immersed in water, after freezing at −20° C., the mineralized three-dimensional porous graphene material was cut into sheets at −10° C., then the mineralized three-dimensional porous graphene sheets were immersed in 75% ethanol, dried, and radiated for sterilization to obtain the bone defect filler.

Embodiment 7

Preparation of a bone defect filler using a mineralized three-dimensional porous graphene material.

The mineralized three-dimensional porous graphene material of the embodiment 5 was immersed in tert-Butyl alcohol, after freezing at −0.1° C., the mineralized three-dimensional porous graphene material was cut into sheets at 5° C., then the mineralized three-dimensional porous graphene sheets were immersed in 75% ethanol, washed with pure ethanol, dried, and radiated for sterilization to obtain the bone defect filler.

Embodiment 8

Preparation of a bone defect filler using a mineralized three-dimensional porous graphene material.

The mineralized three-dimensional porous graphene material of the embodiment 5 was immersed in a 50% aqueous solution of tert-Butyl alcohol, after freezing at −5° C., the mineralized three-dimensional porous graphene material was cut into sheets at 0° C., then the mineralized three-dimensional porous graphene sheets were immersed in 75% ethanol, washed with water, washed with pure ethanol, freeze-dried at low temperature, and radiated for sterilization to obtain the bone defect filler.

According to the clinical requirements, a single sheet is used, or a plurality of sheets are stacked or bonded by a biomedical liquid, for filling bone defects having various shapes.

As compared with a hydroxyapatite biological ceramic that is used as a conventional synthetic bone replacement, when the mineralized three-dimensional graphene sheet is used as a bone defect filler, the biological compatibility, bone conductivity, and osteogenic induction ability are more desirable, and during the culture of mesenchymal stem cells on surface, the proportion of mesenchymal stem cells that differentiate into osteogenic cells is 2 times to 20 times larger, and the differentiation time is earlier by 1.1 times to 5 times.

Compared with a hydroxyapatite biological ceramic (a control group) that is used as a bone defect filling material, when the mineralized three-dimensional porous graphene sheets (an experimental group) are used as bone defect filling materials, in one month to three months after filling in bone defect regions, the bone density changes faster than that in the control group. After three to six months, the bone density in the experimental group can reach 60% to 90% of the original bone density, and the bone density in the control group is only 30% to 60%. The bone density in the experimental group is 1.1 times to 5 times of the bone density in the control group. As observed in a CT image, there is no clear interface in the experimental group, but there is a distinct bone-material interface in the control group.

The above preferred embodiments are described for illustration only, and are not intended to limit the scope of the invention. It should be understood, for a person skilled in the art, that various improvements or variations can be made therein without departing from the spirit and scope of the invention, and these improvements or variations should be covered within the protecting scope of the invention.

What is claimed is:

1. A neural electrode based on a three-dimensional porous graphene foam material, consisting of a current generation device, a first electrode, a second electrode, conductive adhesive, conductive metal wire, a protective substrate, and an insulating protective sleeve; the current generation device being connected to the first electrode and the second electrode through a conductive metal wire respectively,
   wherein at least one of the first electrode and the second electrode is a three-dimensional porous graphene electrode,
   wherein the insulating protective sleeve is disposed directly outside the conductive metal wire, and
   wherein the protective substrate is disposed on one surface of the three-dimensional porous graphene electrode and formed of a polymer material.

2. The neural electrode based on a three-dimensional porous graphene foam material as claimed in claim 1, wherein the protective sleeve is made of silica gel or polyurethane.

3. The neural electrode based on a three-dimensional porous graphene foam material as claimed in claim 1, wherein the conductive metal wire is a silver wire or a copper wire.

4. The neural electrode based on a three-dimensional porous graphene foam material as claimed in claim 1, wherein the conductive metal wire is connected to the three-dimensional porous graphene electrode by a conductive adhesive.

5. The neural electrode based on a three-dimensional porous graphene foam material as claimed in claim 1, wherein the thickness of the protective substrate is 0.1 mm to 2 mm.

6. The neural electrode based on a three-dimensional porous graphene foam material as claimed in claim 1, wherein a thickness ratio of the three-dimensional porous graphene electrode to the protective substrate is 1:0.25 to 1:4.

7. A preparation method of the neural electrode based on a three-dimensional porous graphene foam material as claimed in claim 1, comprising steps of:
   (1) bonding a three-dimensional porous graphene electrode to a conductive metal wire by a conductive adhesive;
   (2) immersing a connecting portion of the conductive metal wire and the three-dimensional porous graphene electrode in a polymer solution, and curing the polymer to form a protective substrate;
   (3) connecting the three-dimensional porous graphene electrode having the protective substrate to another electrode and a current generation device through conductive metal wire to fabricate the neural electrode;
   wherein an insulating protective sleeve is disposed directly outside all conductive metal wire.

* * * * *